United States Patent [19]

VanSlyke

[11] Patent Number: 5,151,629
[45] Date of Patent: Sep. 29, 1992

[54] BLUE EMITTING INTERNAL JUNCTION ORGANIC ELECTROLUMINESCENT DEVICE (I)

[75] Inventor: Steven A. VanSlyke, Rochester, N.Y.

[73] Assignee: Eastman Kodak Company, Rochester, N.Y.

[21] Appl. No.: 738,776

[22] Filed: Aug. 1, 1991

[51] Int. Cl.$^5$ ............................................. H05B 33/26
[52] U.S. Cl. ................................ 313/504; 252/301.16
[58] Field of Search .............. 252/301.16; 546/7; 313/504

[56] References Cited

U.S. PATENT DOCUMENTS

| | | | |
|---|---|---|---|
| 2,864,771 | 12/1958 | Switzer | 252/301.16 |
| 3,163,530 | 12/1964 | Schlesinger | 546/7 |
| 3,567,932 | 3/1971 | Alburger | 546/7 |
| 4,539,507 | 9/1985 | VanSlyke et al. | 313/504 |
| 4,720,432 | 1/1988 | VanSlyke et al. | 428/457 |
| 4,769,292 | 9/1988 | Tang et al. | 428/690 |
| 4,775,820 | 10/1988 | Eguchi | 313/504 |
| 4,885,211 | 12/1989 | Tang et al. | 428/457 |
| 4,950,950 | 8/1990 | Perry et al. | 313/504 |
| 5,047,687 | 9/1991 | Van Slyke | 313/504 |
| 5,059,861 | 10/1991 | Littman | 313/504 |
| 5,059,862 | 10/1991 | Van Slyke | 313/504 |
| 5,061,569 | 10/1991 | Van Slyke | 252/301.16 |
| 5,073,446 | 12/1991 | Scozzafava | 313/504 |

FOREIGN PATENT DOCUMENTS 2-008287 1/1990 Japan .
2-008290 1/1990 Japan .
2-255790 10/1990 Japan .

OTHER PUBLICATIONS

Kushi et al, "The Crystal and Molecular Structure of Bis(2-methyl-8-quinolinolato)aluminum(III)-$\mu$-oxo-bis(2-methyl-8-quinolinolato)aluminium(III)", J. Amer. Chem. Soc., 92(1), pp. 91-96 (1970).

Primary Examiner—Prince Willis, Jr.
Assistant Examiner—Thomas Steinberg
Attorney, Agent, or Firm—Robert Luke Walker

[57] ABSTRACT

An internal junction organic electroluminescent device is disclosed comprised of, in sequence, an anode, an organic hole injecting and transporting zone, an organic electron injecting and transporting zone, and a cathode. The organic electron injecting and transporting zone is comprised of an electron injecting layer in contact with the cathode and, interposed between the electron injecting layer and the organic hole injecting and transporting zone, a blue emitting luminescent layer comprised of a bis($R^s$-8-quinolinolato) aluminum(III)-$\mu$-oxo-bis($R^s$-8-quinolinolato)- aluminum(III), where $R^s$ substituents are chosen to block the attachment of more than two substituted 8-quinolinolato ring nuclei to any one aluminum atom. Increased operating stability and device emission at even shorter blue wavelengths can be realized by the incorporation of a pentacarbocyclic aromatic fluorescent dye.

25 Claims, 2 Drawing Sheets

BLUE EMITTING INTERNAL JUNCTION ORGANIC ELECTROLUMINESCENT DEVICE (I)

FIELD OF THE INVENTION

The invention relates to internal junction organic electroluminescent devices. More specifically, the invention relates to organic electroluminescent devices of the type in which an organic medium contains an internal junction formed at the interface of an electron injecting and transporting zone in contact with a cathode and a hole injecting and transporting zone in contact with an anode.

BACKGROUND OF THE INVENTION

Electroluminescent devices (hereinafter also referred to as EL devices) contain spaced electrodes separated by an electroluminescent medium that emits light in response to the application of an electrical potential difference across the electrodes. Through intensive investigations and a series of recent inventions organic electroluminescent devices of improved characteristics, both in terms of fabrication feasibility and operating performance have been developed.

In current preferred forms organic EL devices are comprised of an anode, an organic hole injecting and transporting zone in contact with the anode, an electron injecting and transporting zone forming a junction with the organic hole injecting and transporting zone, and a cathode in contact with the electron injecting and transporting zone. When an electrical potential is placed across the electrodes, holes and electrons are injected into the organic zones from the anode and cathode, respectively. Light emission results from hole-electron recombination within the device.

A class of organic EL devices that have exhibited highly desirable levels of efficiency and stability are those that have employed a metal oxinoid charge accepting compound to form the electron injecting and transporting zone of the organic EL device. Preferred metal oxinoid compounds have been identified as those that satisfy the formula:

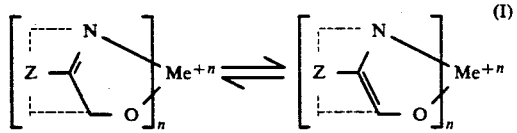

where
Me represents a metal,
n is an integer of from 1 to 3, and
Z represents the atoms necessary to complete an oxine nucleus.

R-1. VanSlyke et al U.S. Pat. No. 4,539,507 discloses in column 9, lines 14 to 16 inclusive, metal complexes of 8-hydroxyquinoline, where the metal is Zn, Al, Mg, or Li. In Example 9 the metal complex is bis(8-hydroxyquinolino)aluminum and in Example 10, bis(8-hydroxyquinolino)magnesium.

R-2. Tang et al U.S. Pat. No. 4,769,292 discloses constructing an organic EL device in which the luminescent layer is comprised of a charge accepting host material and a fluorescent material. The host material can be chosen from among diarylbutadienes, stilbenes, optical brighteners, and metal oxinoid compounds, with the following being listed among preferred embodiments: aluminum trisoxine, magnesium bisoxine, bis[benzo{f}-8-quinolino]zinc, bis(2-methyl-8-quinolinato)aluminum oxide, indium trisoxine, aluminum tris(5-methyloxine), lithium oxine, gallium trisoxine, calcium bis(5-chlorooxine), poly[zinc(II)-bis(8-hydroxy-5-quinolinyl)methane, dilithium epindolidione, 1,4-diphenylbutadiene, 1,1,4,4-tetraphenylbutadiene, 4,4'-bis[5,7-di(t-pentyl-2-benzoxazolyl]stilbene, 2,5-bis[5,7-di(t-pentyl-2-benzoxaolyl]thiophene, 2,2'-(1,4-phenylene-divinylene)bisbenzothiazole, 4,4'-(2,2'-bisthiazolylbiphenyl, 2,5-bis[5-α,α-dimethylbenzyl)-2-benzoxazolyl]thiophene, 2,5-bis[5,7-di(t-pentyl)-2-benzoxazolyl]-3,4-diphenylthiophene, and trans-stilbene.

R-3. VanSlyke et al U.S. Pat. No. 4,720,432 discloses organic EL devices in which the organic hole injecting and transporting zone is comprised of a layer in contact with the anode containing a hole injecting porphyrinic compound and a layer containing a hole transporting aromatic tertiary amine interposed between the hole injecting layer and the electron injecting and transporting zone. The metal oxinoid charge accepting compounds are those disclosed to form the electron injecting and transporting zone in R-2.

R-4. Tang et al U.S. Pat. No. 4,885,211 discloses organic EL devices with improved cathodes containing a metal oxinoid compound in the electron injecting and transporting zone. The metal oxinoid charge accepting compounds are those disclosed to form the electron injecting and transporting zone in R-2.

R-5. Perry et al U.S. Pat. No. 4,950,950 discloses organic EL devices in which the hole injecting and transporting zone is comprised of (a) a layer in contact with the anode containing a hole injecting porphyrinic compounds and (b) a layer containing a hole transporting silazane interposed between the hole injecting layer and the electron injecting and transporting zone. The metal oxinoid charge accepting compounds are those disclosed to form the electron injecting and transporting zone in R-2. Aluminum oxinate is set out in the Examples.

R-6. Kushi et al, "The Crystal and Molecular Structure of Bis(2-methyl-8-quinolinolato)aluminum(III)-μ-oxo-bis(2-methyl-8-quinolinolato)aluminum(III)", J. Amer. Chem. Soc., 92(1), pp.91–96 (1970), discloses the preparation of the title and similar compounds.

Related Patent Applications (RPA-1) VanSlyke et al U.S. Pat. No. 5,059,862, filed Jul. 26, 1990, commonly assigned, ELECTROLUMINESCENT DEVICE WITH IMPROVED CATHODE discloses an internal junction organic electroluminescent device comprised of, in sequence, an anode, an organic hole injecting and transporting zone, an organic electron injecting and transporting zone forming a junction with the organic hole injecting and transporting zone, and a cathode comprised of a layer contacting the organic electron injecting and transporting zone containing a combination of magnesium and aluminum, with aluminum accounting for at least 80 percent of the cathode layer. The metal oxinoid charge accepting compounds are those disclosed to form the electron injecting and transporting zone in R-2.

(RPA-2) Littman et al U.S. Pat. No. 5,059,861, filed Jul. 26, 1990, commonly assigned, ORGANIC ELECTROLUMINESCENT DEVICE WITH STABILIZING CATHODE CAPPING LAYER discloses an organic electroluminescent device comprised of, in sequence, a support, an anode, an organic electroluminescent medium, and cathode containing a plurality of metals other than alkali metals. The cathode is comprised of a capping layer containing at least one alkaline earth or rare earth metal and an electron injecting layer containing at least one metal having a work function of less than 4.0, but a higher work function than the alkaline earth or rare earth in the capping layer. The metal oxinoid charge accepting compounds are those disclosed to form the electron injecting and transporting zone in R-2.

(RPA-3) VanSlyke U.S. Pat. No. 5,047,687, filed Jul. 26, 1990, commonly assigned, ORGANIC ELECTROLUMINESCENT DEVICE WITH STABILIZED CATHODE discloses an organic electroluminescent device comprised of, in sequence, a support, an anode, an organic electroluminescent medium, and a cathode. The cathode is comprised of a layer containing a plurality of metals (other than alkali metals) having a work function of less than 4 eV. A protective layer overlies the cathode and is comprised of a mixture of at least one organic component of the organic electroluminescent medium and at least one metal having a work function in the range of from 4.0 to 4.5 capable of being oxidized in the presence of ambient moisture. The metal oxinoid charge accepting compounds are those disclosed to form the electron injecting and transporting zone in R-2.

(RPA-4) Scozzafava et al U.S. Pat. No. 5,073,446, filed Jul. 26, 1990, commonly assigned, ORGANIC ELECTROLUMINESCENT DEVICE WITH STABILIZING FUSED METAL PARTICLE CATHODE discloses an organic electroluminescent device comprised of, in sequence, an anode an organic electroluminescent medium, and a cathode consisting essentially of a plurality of metals other than alkali metals, at least one of the metals having a work function less than that of indium. The cathode is comprised of a layer of fused metal particles containing at least 80 percent indium and having a mean diameter of less than 1 $\mu$m and a coefficient of variation of less than 20 percent. The metal oxinoid charge compounds are those disclosed to form the electron injecting and transporting zone in R-2.

(RPA-5) VanSlyke et al U.S. Ser. No. 561,552, filed Jul. 26, 1990, commonly assigned, ELECTROLUMINESCENT DEVICE WITH ORGANIC ELECTROLUMINESCENT MEDIUM discloses an internal junction organic electroluminescent device comprised of, in sequence, an anode, an organic hole injecting and transporting zone comprised of a layer containing a hole transporting aromatic tertiary amine, an organic electron injecting and transporting zone, and a cathode. The hole transporting aromatic tertiary amine is comprised of at least two tertiary amine moieties and includes attached to a tertiary amine nitrogen atom an aromatic moiety containing at least two fused aromatic rings. The metal oxinoid charge accepting compounds are those disclosed to form the electron injecting and transporting zone in R-2.

(RPA-6) VanSlyke et al U.S. Ser. No. 07/738,777, concurrently filed and commonly assigned, IMPROVED BLUE EMITTING INTERNAL JUNCTION ORGANIC ELECTROLUMINESCENT DEVICE (I) discloses an internal junction organic EL device comprised of, in sequence, an anode, an organic hole injecting and transporting zone, an organic electron injecting and transporting zone, and a cathode. The organic electron injecting and transporting zone is comprised of an electron injecting layer in contact with the cathode and, interposed between the electron injecting layer and the organic hole injecting and transporting zone, a blue emitting luminescent layer comprised of an aluminum chelate containing a phenolato ligand and two $R^28$-quinolinolato ligands, where Rs substituents are chosen to block the attachment of more than two substituted 8-quinolinolato ring nuclei to the aluminum atom. The presence of the phenolato ligand shifts device emission to the blue region of the spectrum and increases emission efficiency. Device emission at even shorter blue wavelengths and increased operating stability can be realized by the incorporation of a pentacarbocyclic aromatic fluorescent dye.

SUMMARY OF THE INVENTION

In constructing organic EL devices initial investigation objectives were directed toward identifying materials for constructing the organic medium that would yield attractive levels of efficiency and stability and exhibit electroluminescence with relatively low levels of applied voltage. The best realization of these objectives has been achieved by choosing metal oxinoid compounds satisfying formula I above to form the electron injecting and transporting zone of organic EL devices.

As these initial investigation objectives have been satisfied interest has turned toward constructing organic EL devices capable of providing electroluminescence in the desired portion of the visible spectrum. The inferior performance of organic EL devices emitting in the blue portion of the spectrum has drawn particular interest.

It is an object of the invention to provide a blue emitting organic EL device exhibiting an improved emission efficiency. It is particularly contemplated to provide organic EL devices that exhibit performance efficiencies exceeding those of the best green emitting organic EL devices employing metal oxinoid compounds as emitters. Metal oxinoid compounds satisfying formula I have produced the best green emitting organic EL devices; however, it has not been previously recognized how the advantages of these materials could be improved upon or even matched while achieving blue electroluminescence.

It is another object of this invention t provide a blue emitting organic EL device which exhibits both a high level of efficiency and a high level of stability as compared to conventional blue emitting organic EL devices. It is a further object to provide a blue emitting organic EL device that is shifted in its emission to shorter blue wavelengths.

In one aspect, this invention is directed to an internal junction organic electroluminescent device comprised of, in sequence, an anode, an organic hole injecting and transporting zone, an organic electron injecting and transporting zone, and a cathode.

The organic electroluminescent device is characterized in that the organic electron injecting and transporting zone is comprised of an electron injecting layer in contact with the cathode and, interposed between the electron injecting layer and the organic hole injecting and transporting zone, a blue emitting luminescent layer comprised of a charge accepting compound of the formula:

$$(R^5-Q_2-Al-O-Al-(Q-R^5)_2 \quad (II)$$

where

Q in each occurrence represents a substituted 8-quinolinolato ring nucleus and $R^s$ represents an 8-quinolinolato ring substituent chosen to block sterically the attachment of more than two substituted 8-quinolinolato ring nuclei to any one aluminum atom.

DESCRIPTION OF PREFERRED EMBODIMENTS

The present invention is directed to a blue emitting organic EL device that exceeds the performance efficiencies of conventional green emitting organic EL devices.

The terms "blue emitting" and "green emitting" are easy enough to understand and identify in most instances; but since there is a continuous spectrum of hues ranging from pure blue to pure green, a quantitative basis is required for precise delineation. This quantitative basis is provided by the 1931 C.I.E. chromaticity diagram shown in FIG. 1. The 1931 C.I.E. chromaticity diagram is a widely accepted approach for quantifying hue within the visible spectrum. A full explanation of the 1931 C.I.E. chromaticity diagram is provided by Wyszecki and Stiles, *Color Science, Concepts and Methods: Quantitative Data and Formulae*, 2nd Ed., Chapter 3, Colorimetry, Wiley, 1982, pp. 117–143, and a more succinct explanation is provided by James, *The Theory of the Photographic Process*, 4th Ed., Macmillan, 1977, Chapter 19, II, B. Colorimetry, pp. 563–565.

Figure 1:
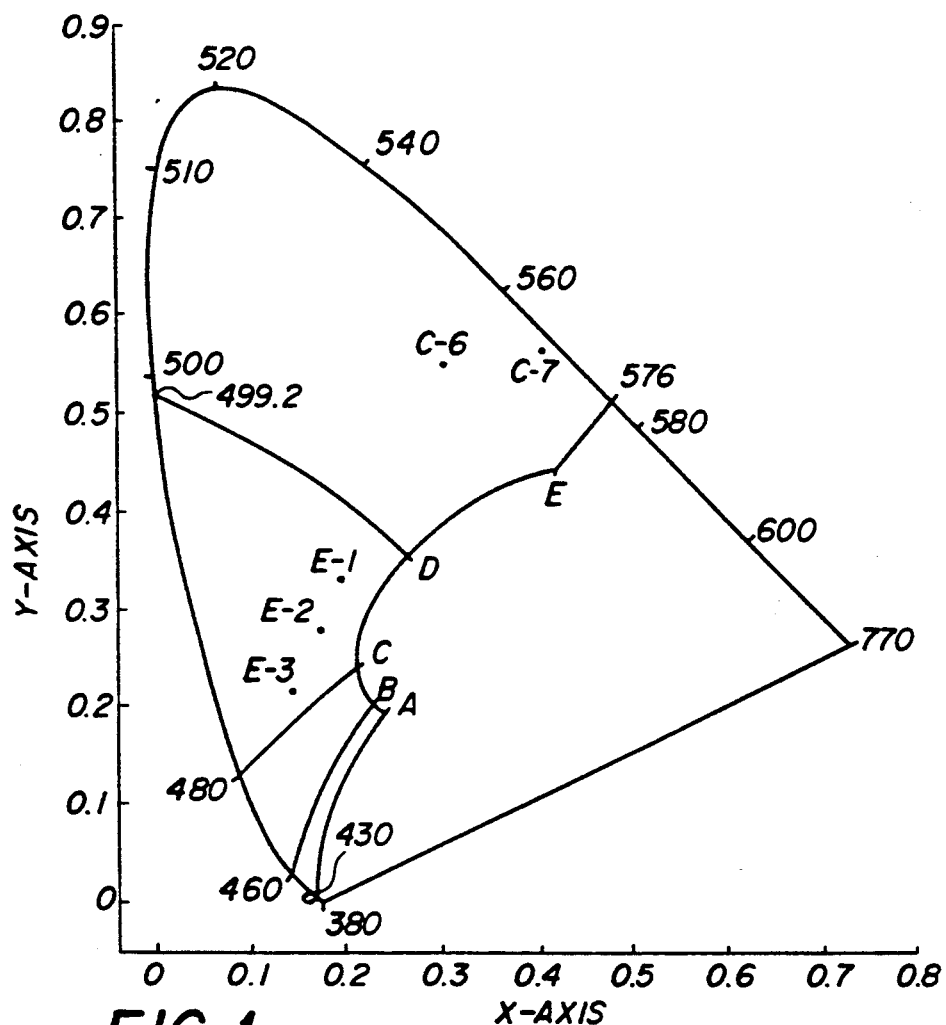
FIG. 1 is a 1931 C.I.E. chromaticity diagram with color regions of specific interest delineated.

Referring to FIG. 1, fully saturated monochromatic hues ranging from 380 to 770 nm form a curve defining the saturation boundaries of the visible spectrum. Hues that lie within the curve boundary are to some extent desaturated, meaning that they tend more toward white. The x and y axes are employed as descriptors for precisely locating each visible hue.

As herein employed the term "blue emitting" refers to the area of the diagram defined by the points extending from 430 to 499.2 nm to D, C, B and A and back to 430 nm. The area extending from 460 to 480 nm to C to B and back to 460 nm is perceived by the eye as being blue. The area extending from 430 to 460 nm to B to A and back to 430 nm is perceived by the eye as being bluish purple. The area extending from 480 to 99.2 nm to D to C and back to 480 nm is perceived by the eye as being greenish blue or bluish green. The area to right of points A, B, C and D are excluded, since the hue is so desaturated that the visual perception is primarily that of white.

As herein employed the term "green emitting" refers to the area of the diagram defined by the points extending from 499.2 to 576 nm to E and D and back to 99.2 nm. It is in this area of the spectrum that conventional green emitting organic EL devices emit. To the right of the boundary defined by 499.2 and D the observed hue is green while the left of the boundary defined by 576 and E the observed hue is greenish yellow.

Figure 2:
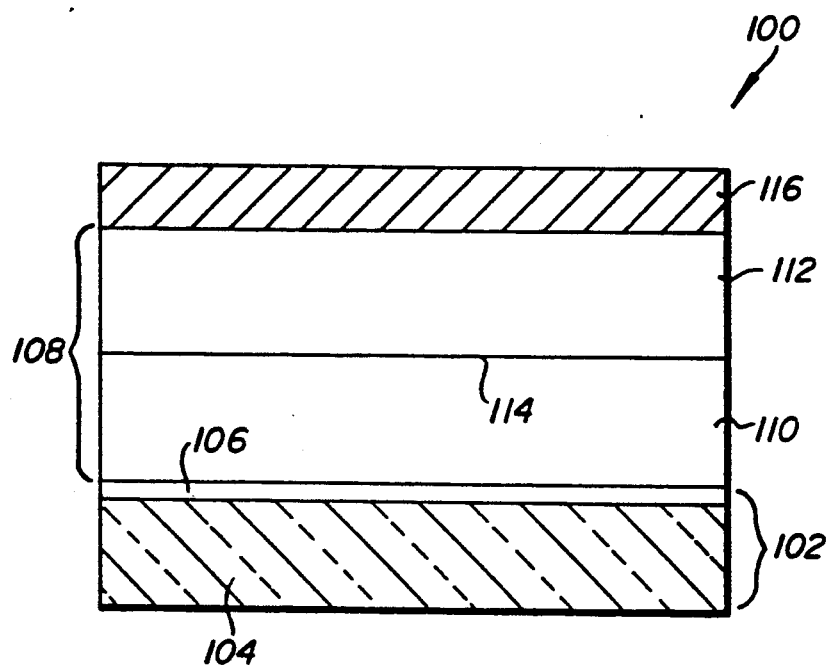
FIG. 2 is a schematic diagram of a conventional green emitting organic EL device.

A conventional green emitting organic EL device 100 is shown in FIG. 2. An anode 102 of the device is shown constructed of a transparent support 104 and a thin transparent conductive layer 106. Overlying and in contact with the anode is an organic medium 108 formed by a hole injecting and transporting zone 110 in contact with the anode and an electron injecting and transporting zone 112 forming a junction 114 with the zone 110. The electron injecting and transporting zone is in contact with a cathode 116.

In operation, when the cathode 116 is electrically biased to a negative potential with respect to the anode 102 holes are injected into the organic hole injecting and transporting zone 110 at its interface with the anode and transported across this zone to the junction 114. Concurrently electrons are injected into the electron injecting and transporting zone 112 at its interface with the cathode 116, and the injected electrons are transported toward the junction 114. Recombination of the holes and electrons occurs within the electron injecting and transporting zone adjacent the junction 114 resulting in electroluminescence within the electron injecting and transporting zone. The hue of the luminescence is determined by the composition of the electron injecting and transporting zone. The light emitted can leave the organic EL device in any direction—i.e., through the edges of the organic medium, the cathode and/or the anode. In the construction shown, which is most common, principal emission occurs through the transparent anode.

While the electron injecting and transporting zone 112 of the conventional organic EL device 100 can take any of the varied forms disclosed in R-1, R-2, R-3, R-4 and R-5 (hereinafter referred to collectively as R-1-5), best performance is realized when the zone 112 employs a metal oxinoid charge accepting compound satisfying the formula:

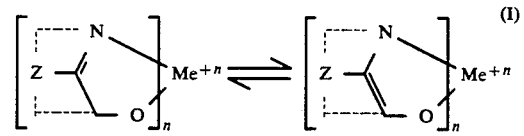

where
Me represents a metal,
n is an integer of from 1 to 3, and
Z represents the atoms necessary to complete an oxine nucleus.

Illustrative of useful chelated oxinoid compounds are the following:

CO-1: Aluminum trisoxine
CO-2: Magnesium bisoxine
CO-3: Bis[benzo{f}-8-quinolinolato]zinc
CO-4: Aluminum tris(5-methyloxine)
CO-6: Lithium oxine
CO-7: Gallium tris(5-chlorooxine)
CO-8: Calcium bis(5-chlorooxine)
CO-9: Poly[zinc (II)-bis(8-hydroxy-5-quinolinyl)methane]
CO-10: Dilithium epindolidione
CO-11: Aluminum tris(4-methyloxine)
CO-12: Aluminum tris(6-trifluoromethyloxine)

Of the various metal oxinoids, the most highly preferred are the tris-chelates of aluminum. These chelates are formed by reacting three 8-hydroxyquinoline moieties with a single aluminum atom. The specific examples of such aluminum compounds provided in R-1-5 are aluminum trisoxine [a.k.a., tris(8-quinolinol) aluminum] and aluminum tris(5-methyloxine) a.k.a. tris(5-methyl-8-quinolinol) aluminum]. These aluminum trisoxines are green emitting.

The present invention is directed to the discovery of an organic EL device construction that improves on the efficiencies of conventional green emitting aluminum trisoxines used to form an electron injecting and transporting zone, but produces a blue emitting organic EL device.

Figure 3:
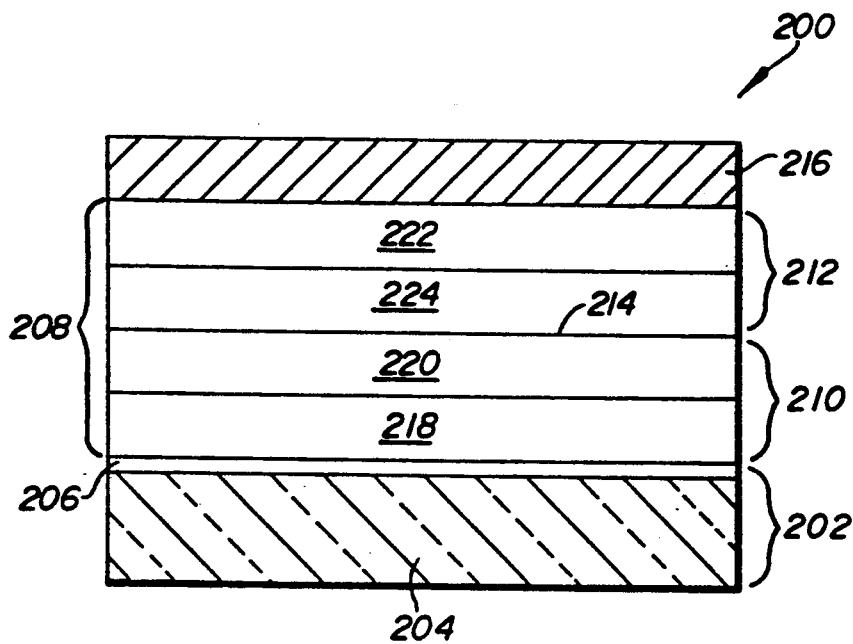
FIG. 3 is a schematic diagram of a blue emitting organic EL device satisfying the requirements of the invention.

A preferred blue emitting organic EL device 200 satisfying the requirements of the invention is shown in FIG. 3. The anode 202 is in its preferred form constructed of a transparent support 204 and a conductive layer 206 similarly as conventional anode 102 described above. The cathode 216 can also be identical to conventional cathode 116.

An organic medium 208 contacting each of the anode and cathode and extending therebetween consists of a hole injecting and transporting zone 210 and an electron injecting and transporting zone 212. A junction 214 is formed at the interface of the zones 210 and 212.

The hole injecting and transporting zone 210 can take any convenient conventional form and can, if desired, be formed of a single material, similarly as corresponding zone 110. In the preferred construction shown the hole injecting and transporting zone consists of a hole injecting layer 218 in contact with the anode and a contiguous hole transporting layer 220 interposed between the hole injecting layer and the electron injecting and transporting zone. Unitary and two layer hole injecting and transporting zones are illustrated by R-1-5, cited above and here incorporated by reference. A particularly preferred hole transporting layer 220 contains a hole transporting aromatic tertiary amine comprised of at least two tertiary amine moieties and includes attached to a tertiary amine nitrogen atom an aromatic moiety containing at least two fused aromatic rings. Such hole transporting aromatic tertiary amines, more fully described below, are the subject of copending, commonly assigned VanSlyke et al U.S. Pat. No. 561,552, filed Jul. 26, 1990, titled ELECTROLUMINESCENT DEVICE WITH ORGANIC ELECTROLUMINESCENT MEDIUM.

The electron injecting and transporting zone 212 is formed of an electron injecting layer 222, which is in contact with the cathode, and a contiguous electron transporting layer 224 that is interposed between layer 222 and the hole injecting and transporting zone 210. The electron transporting layer forms a 3unction 214 with the hole injecting and transporting zone 210.

The electron injecting layer can be formed of any of the materials conventionally employed to form the electron injecting and transporting zone 112. For example, the electron injecting layer can be formed of any of the materials used to form the electron injecting and transporting zones of the organic EL devices disclosed in any of R-1-5, the disclosures of which are here incorporated by reference. It is particularly preferred that the electron injecting layer be formed of a metal oxinoid compound satisfying formula I and it is most preferred that the metal oxinoid compound be an aluminum trisoxinoid compound.

The electron transporting layer is comprised of a blue emitting bis($R^5$8-quinolinolato)aluminum(III)-$\mu$-oxo-bis($R^5$8-quinolinolato)aluminum(III) serving as a charge accepting compound, where $R^5$ is a ring substituent of the 8-quinolinolato ring nucleus chosen to block the attachment of more than two 8-quinolinolato nuclei to any one aluminum atom. These compounds can be represented by the formula:

$$(R^5-Q)_2-Al-O-Al-(Q-R^5)_2 \quad (II)$$

where

Q in each occurrence represents a substituted 8-quinolinolato ring nucleus and $R^5$ represents an 8-quinolinolato ring substituent chosen to block sterically the attachment of more than two substituted 8-quinolinolato ring nuclei to any one aluminum atom.

Although either or both of the 8-quinolinolato rings can contain substituents other than the steric blocking substituent, further substitution of the rings is not required to realize a blue emitting organic EL device. It is appreciated further that more than one substituent per ring can contribute to steric blocking. The various steric blocking substituent possibilities are most easily visualized by reference to the following formula:

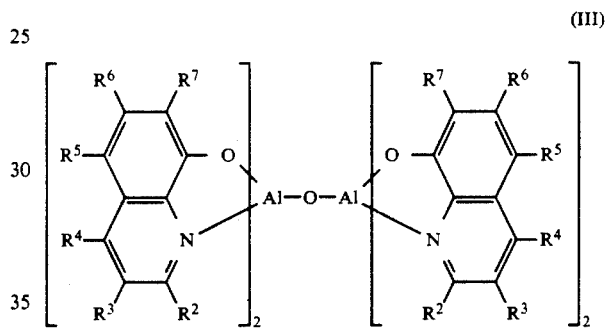

(III)

where $R^2$ to $R^7$ represent substitutional possibilities at each of ring positions 2 to 7 inclusive of the 8-quinolinolato rings. Substituents at the 4, 5 and 6 ring positions are not favorably located to hinder sterically the bonding of three 8-quinolinolato nuclei to a single aluminum atom. While it is contemplated that large substituents at the 3 or 6 ring positions could provide sufficient steric hindrance, the incorporation of bulky substituents substantially increases molecular weight without enhancing molecular performance and therefore detracts from overall performance. On the other hand, the 2 ring position is ideally suited to provide steric hindrance, and even a very small substituent (e.g., a methyl group) in this ring position provides an effective steric blocking substituent. For synthetic convenience it is specifically preferred that the steric blocking substituent be located in the 2 ring position. As employed herein the term "steric blocking" is employed to indicate that the $R^5$-Q ligand is incapable of competing for inclusion as the third ligand of the aluminum atom.

It has been discovered quite surprisingly that substituents to the 8-quinolinolato rings can also perform useful hue shifting functions. The quinoline ring consists of fused benzo and pyrido rings. When the pyrido ring component of the quinoline ring is substituted with one or more electron donating substituents the effect is to shift hue of emission away from the axis 499.2-D in FIG. 1 and toward the axis 480-C. That is, emission is shifted away from the green region of the spectrum and toward a more primary blue emission. Electron donating substituents at the ortho and para positions of the pyrido ring (that is, the 2 and 4 positions of the quinoline ring) particularly influence the hue of emission, while the meta position on the pyrido ring (the 3 position on the quinoline ring) has a comparatively small influence on the hue of emission. It is, in fact, recognized that an electron accepting substituent could, if desired, be located at the 3 ring position while retaining a blue emission characteristic. Although steric hindrance is entirely independent of electron donating or accepting properties and, thus, $R^2$ can in theory take the form of either an electron donating or accepting group, it is preferred to choose $R^2$ from among electron donating groups. By adding a second electron donating group $R^4$ a further shift in hue away from the green portion of the spectrum is achieved. $R^3$, when present, can take any synthetically convenient form, but is preferably also electron donating.

By contrast electron accepting substituents of the benzo ring component of the quinoline nucleus shift the hue of emission away from axis 499.2-D and toward axis 480-C in FIG. 1. Thus, any or all of substituents at the 5, 6 and 7 quinoline ring positions, when present, are preferably electron accepting.

It is well within the skill of the art to determine whether a particular substituent is electron donating or electron accepting. The electron donating or accepting properties of several hundred of the most common substituents, reflecting all common classes of substituents have been determined, quantified and published. The most common quantification of electron donating and accepting properties is in terms of Hammett $\sigma$ values. Substituents with negative Hammett $\sigma$ values are electron donating while those with positive Hammett $\sigma$ values are electron accepting. Hydrogen has a Hammett $\sigma$ value of zero, while other substituents have Hammett o values that increase positively or negatively in direct relation to their electron accepting or donating characteristics. Lange's Handbook of Chemistry, 12th Ed., McGraw Hill, 1979, Table 3-12, pp. 3-134 to 3-138, here incorporated by reference, lists Hammett $\sigma$ values for a large number of commonly encountered substituents. Hammett $\sigma$ values are assigned based on phenyl ring substitution, but they provide a workable guide for qualitatively selecting electron donating and accepting substituents for the quinoline ring.

Taking all factors together, steric blocking, synthetic convenience, and electron donating or accepting properties, $R^2$ is preferably an amino, oxy or hydrocarbon substituent. Adequate steric hindrance is provided when $R^2$ is methyl and is the sole 8-quinolinolato ring substituent (i.e., each of $R^3$, $R^4$, $R^5$, $R^6$ and $R^7$ is hydrogen). Thus, any amino, oxy or hydrocarbon substituent having at least 1 carbon atom falls within the perview of preferred substituents. Preferably no more than 10 carbon atoms are present in any one hydrocarbon moiety and optimally no more than 6 carbon atoms. Thus, $R^2$ preferably takes the form of —R', —OR' or —N(R")R', where R' is a hydrocarbon of from 1 to 10 carbon atoms and R" is R' or hydrogen. Preferably $R^2$ contains 10 or fewer carbon atoms and optimally 6 or fewer carbon atoms.

$R^3$ and $R^4$ for the reasons set forth above can take a broader range of forms than $R^2$, but are specifically contemplated to be selected from among the same group of preferred substituents as $R^2$. Since 3 and 4 ring position substitution is not required. $R^3$ and $R^4$ can additionally be hydrogen.

Since 5, 6 or 7 ring position substitution is not required, $R^5$, $R^6$ and $R^7$ can represent hydrogen. In preferred forms $R^5$, $R^6$ and $R^7$ can be selected from synthetically convenient electron accepting substituents, such as cyano, halogen, and α-haloalkyl, α-haloalkoxy, amido, sulfonyl, carbonyl, carbonyloxy and oxycarbonyl substituents containing up to 10 carbon atoms, most preferably 6 or fewer carbon atoms.

The following constitute specific examples of preferred compounds satisfying formula III:

BA-1 Bis(2-methyl-8-quinolinolato)aluminum(III)-μ-oxo-bis(2-methyl-8-quinolinolato)aluminum(III)

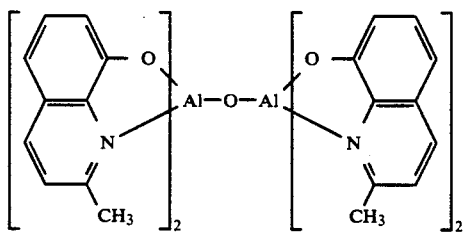

BA-2 Bis(2,4-dimethyl-8-quinolinolato)aluminum(III)-μ-oxo-bis(2,4-dimethyl-8-quinolinolato)-aluminum(III)

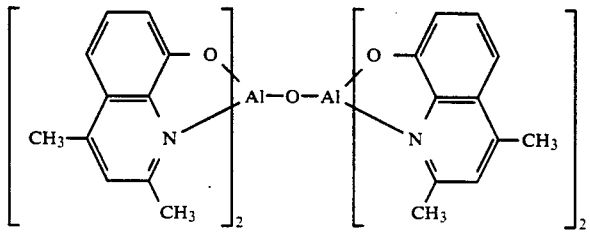

BA-3 Bis(4-ethyl-2-methyl-8-quinolinolato)aluminum(III)-μ-oxo-bis(4-ethyl-2-methyl-8-quinolinolato)aluminum(III)

-continued

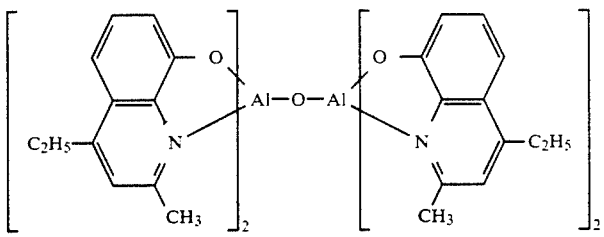

BA-4 Bis(2-methyl-4-methoxyquinolinoato)aluminum(III)-
μ-oxo-bis(2-methyl-4-methoxyquinolinolato)aluminum(III)

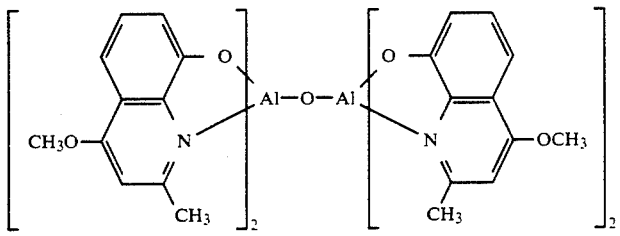

BA-5 Bis(5-cyano-2-methyl-8-quinolinolato)aluminum(III)-
μ-oxo-bis(5-cyano-2-methyl-8-quinolinolato)aluminum(III)

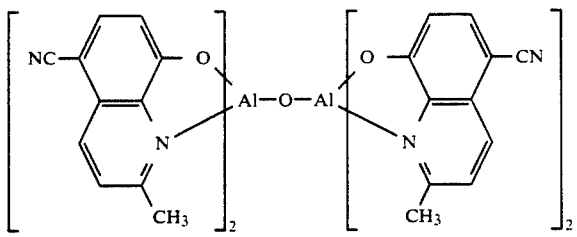

BA-6 Bis(2-methyl-5-trifluoromethyl-8-quinolinolato)aluminum(III)-
μ-oxo-bis(2-methyl-5-trifluoromethylquinolinolato)aluminum(III)

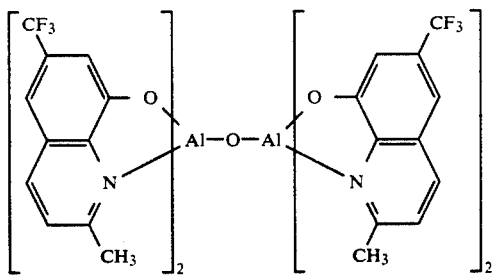

If organic EL device 200 is modified by omitting the electron transporting layer 224, it has desirable performance properties; however, the organic EL device is green emitting, not blue emitting. If the electron injecting layer 222 is omitted so that layer 224 forms the electron injecting and transporting zone in its entirety, a blue emitting organic EL device is formed, but its operating efficiency is markedly reduced.

It has been discovered that blue emitting characteristics and increased operating efficiencies imparted to organic EL devices when blue emitting formula II materials are used to form the electron transporting layer 224 in combination with conventional electron injecting and transporting materials used to form the electron injecting layer 222. By employing the formula II material to form the interface 214 with the hole injecting and transporting zone and keeping the electron injecting layer 224 out of direct contact with the hole injecting and transporting zone the hue of emission from the organic EL device is controlled by the formula II material lying along the junction. If the material of formula II comes in direct contact with the cathode 216, the operating efficiency of the organic EL device is markedly decreased. On the other hand, when a conventional material, such as a formula I material, is employed to form the electron injecting layer 222 and a formula II is employed to form the electron transporting layer 224, the operating efficiency is surprisingly and markedly more efficient than when a conventional green emitting material is employed to form the entire electron injecting and transporting zone.

It is specifically contemplated to incorporate in the electron transporting layer 224 a fluorescent dye following the teachings of Tang et al U.S. Pat. 4,769,292, cited above (R-2), the disclosure of which is here incorporated by reference. Any blue emitting combination of one or more fluorescent dyes and one or more compounds satisfying formula II can be employed. Three distinctly different categories of combinations are possible that permit blue emission:

In a first category, a luminescent electron transporting layer can be constructed by combining a charge accepting compound satisfying formula II as a host compound for a blue emitting fluorescent dye chosen to provide a favored recombination site for holes and electrons. In this arrangement the host and fluorescent dye relationship taught by Tang et al (R-2) is present. In this relationship the compounds of formula II serve as collectors for charge (holes and electrons) accepted into the luminescent layer with the wavelength of emission being controlled by the fluorescent dye. When this relationship is favored the fluorescent dye exhibits a reduction potential less negative than that of the host compound, the fluorescent dye exhibits a lower bandgap potential than that of the host compound, and the host compound and fluorecent dye are spectrally coupled--that is, the host compound has a capability when used alone to emit at a wavelength that corresponds to an absorption wavelength of the fluorescent dye. For optimum coupling it is preferred that the peak emission wavelength of the host correspond to the peak absorption wavelength of the fluorescent dye within ±100 nm, optimally ±25 nm. Blue emitting fluorescent dyes are required in this instance, since the hue of emission is entirely determined by the fluorescent dye.

In a second category the relationships and roles of the formula II compound and the fluorescent dye are simply reversed. The fluorescent dye acts as the host compound while the formula II compound is responsible for blue emission. For this relationship to be favored the formula II compound exhibits a reduction potential less negative than that of the host compound, the formula II compound exhibits a lower bandgap potential than that of host compound, and the host compound and formula II compound are spectrally coupled--that is, the host compound has a capability when used alone to emit at a wavelength that corresponds to an absorption wavelength of the formula II compound. For optimum coupling it is preferred that the peak emission wavelength of the host correspond to the peak absorption wavelength of the formula II compound within ±100 nm, optimally ±25 nm.

When neither of the first and second category conditions are sufficiently satisfied to allow emission solely from the fluorescent dye or the formula II compound, as contemplated by the first and second categories above, respectively, a third category is present in which each of the fluorescent dye and the formula II compounds emits at the same wavelength it emits in the absence of the other. In this instance it is preferred that both the formula II compound and the fluorescent dye be blue emitting.

By choosing a fluorescent dye having a peak emission. at a shorter wavelength than that of formula II compound a shift to shorter wavelength organic EL device emissions can be realized in either of the first or third categories of constructions.

It has been discovered quite unexpectedly that by employing a fluorescent dye having a chromophoric unit containing at least 5 fused carbocyclic aromatic rings (hereinafter referred to as a pentacarbocyclic aromatic fluorescent dye) increased stability of organic EL device operation is achieved and a shift to shorter wavelengths of blue emission can be realized. Operating efficiency and stability are significantly improved in this arrangement as compared to an organic EL device in which the entire electron injecting and transporting zone is constructed of a formula II compound, while lower stabilities and higher operating efficiencies are observed when the electron injecting layer is a formula I compound and the electron transporting layer contains a formula II compound lacking a fluorescent dye.

In one preferred form of the invention the organic EL device is a first category construction in which the electron transporting layer 224 contains a formula II compound as a host and at least one pentacarbocylic aromatic fluorescent dye.

These pentacarbocyclic aromatic fluorescent dyes have been discovered to be highly advantageous for reducing the wavelength of organic EL device emission. To function in a first category arrangement it is essential that the fluorescent dye absorb at a wavelength corresponding to an emission wavelength of the host compound, in this instance the formula II compound. On the other hand, it is recognized that all fluorescent dyes emit at a longer wavelength than they absorb. Stated another way, a dye cannot emit light of a higher energy level than its absorbs. The difference between the longest wavelength absorption maxima (hereinafter referred to as the peak absorption) and the shortest wavelength emission maxima (hereinafter referred to as the peak emission) of a fluorescent dye is known as its Stokes shift. If the Stokes shift of a fluoescent dye is large, it is difficult to achieve efficient spectral coupling and still achieve peak emission at a shorter wavelength than that of the formula II compound. Pentacarbocyclic aromatic fluorescent dyes are particularly suited for shifting organic EL device emissions to shorter blue wavlengths, since they exhibit Stokes shifts of from 80 nm to less than 20 nm, attributable to their relatively rigid chromophoric units. Thus, a hypsochromic shift in organic EL device emission can be realized even though the absoption peak of the pentacarbocyclic aromatic fluorescent dye is only 20 nm shorter in wavelength than the emission peak of the formula II charge carrier compound. Preferred pentacarbocyclic aromatic fluorescent dyes are those that exhibit an absorption peak at wavelengths ranging from 100 to 20 nm shorter than the emission peak exhibited by the formula II charge carrier compound.

The pentacarbocyclic aromatic fluorescent dyes contemplated each contain at least 5 fused carbocyclic aromatic rings, which form a chromophoric unit. Fused aromatic carbocyclic rings in addition to the 5 required fused rings do not detract fro mperformance characteristics. Preferred chromophoric units contain a perylene, benzopyrene, benzochrysene, benzonaphthacene, picene, pentaphene, pentacene, hexacene or anthanthrene nucleus, as the entire nucleus or fused with other aromatic rings to complete the nucleus. Typically these dyes contain from 20 to 40 ring carbon atoms. The following is a listing of fused carbocyclic ring compounds that can form the entire dye or a chromophoric unit of a dye contemplated for use in the practice of the invention:

FD-1 Perylene

-continued
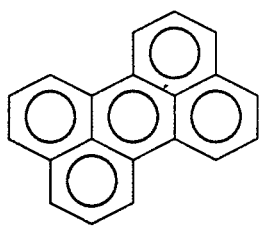
FD-2 Benzo[b]perylene
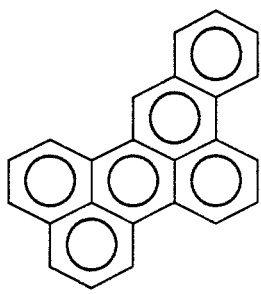
FD-3 Dibenzo[b,pqr]perylene
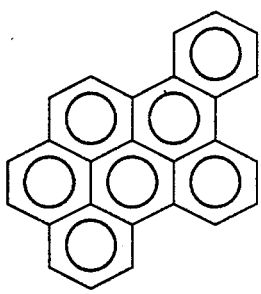
FD-4 Tribenzo[fg,hi,st]pentacene
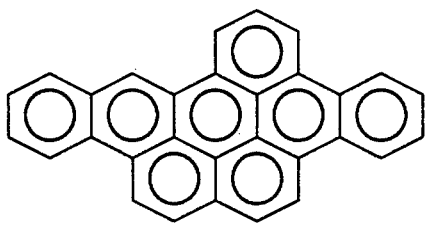
FD-5 Dibenzo[fg,qr]pentacene
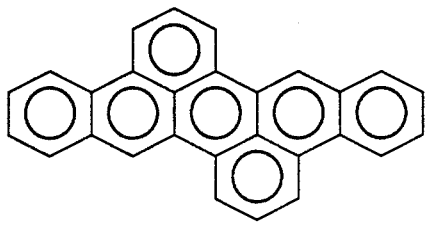
FD-6 Dibenzo[fg,ij]pentaphene
-continued
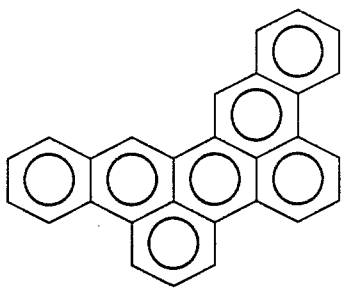
FD-7 Benzo[pqr]perylene
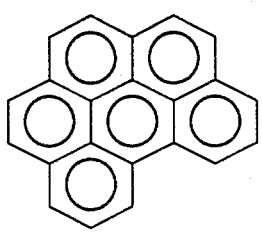
FD-8 Dibenzo[ij,rst]pentaphene
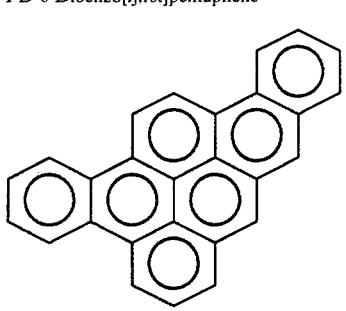
FD-9 Tribenzo[b,ghi,n]perylene
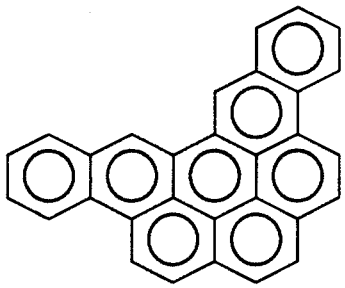
FD-10 Tribenzo[cd,fg,l]pyrene
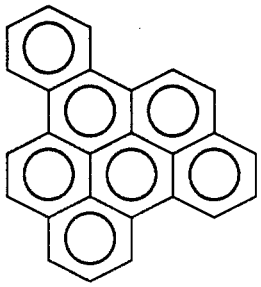
FD-11 Tetrabenzo[a,b,cd,pq]naphthacene

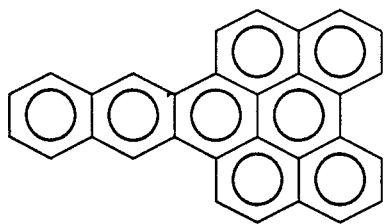
FD-12 Pentabenzo[b,e,h,jk,mn]pyrene
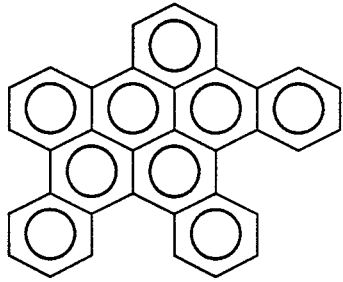
FD-13 Tetrabenz[a,cd,fg,n]anthanthrene
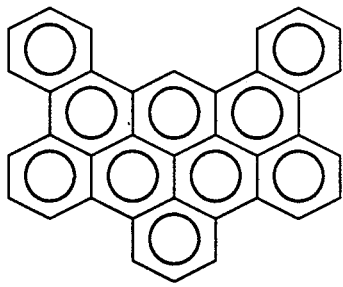
FD-14 Tetrabenz[b,hi,k,qr]anthanthrene
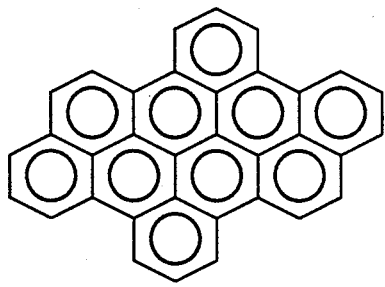
FD-15 Benzo[a]pyrene
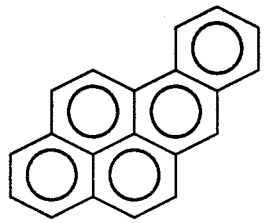
FD-16 Dibenzo[b,d]pyrene
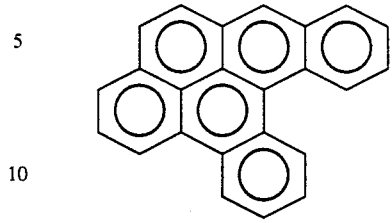
FD-17 Dibenzo[a,e]pyrene
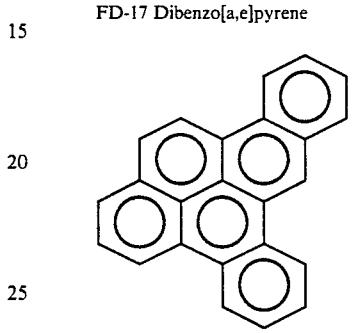
FD-18 Dibenzo[b,h]pyrene
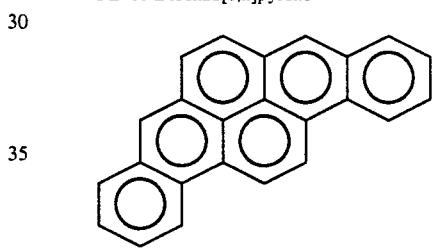
FD-19 Tribenzo[a,e,i]pyrene
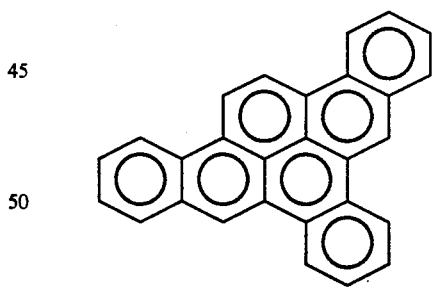
FD-20 Tribenzo[b,e,h]pyrene
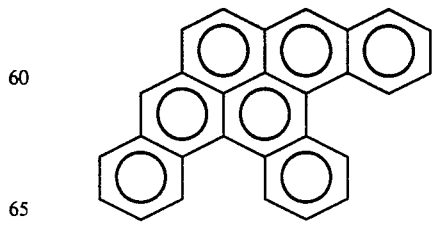
FD-21 Dibenzo[e,l]pyrene

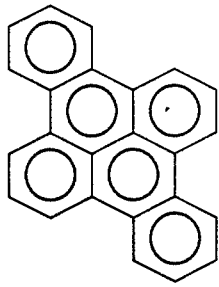

FD-22 Dibenzo[a,h]pyrene

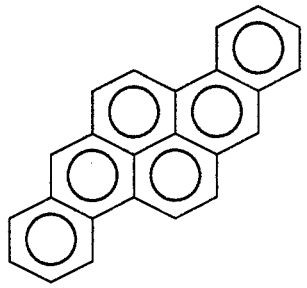

FD-23 Dibenzo[b,mn]chrysene

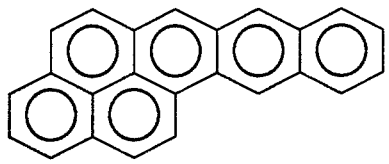

FD-24 Dibenzo[de,qr]napthacene

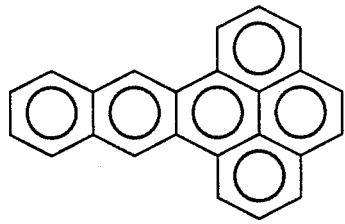

FD-25 Dibenzo[c,mn]chrysene

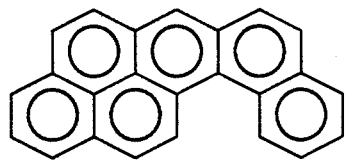

FD-26 Tetrabenzo[hi,j,k,qr]anthanthrene

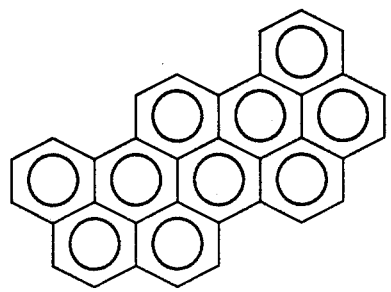

FD-27 Tribenzo[a,c,de]naphthacene

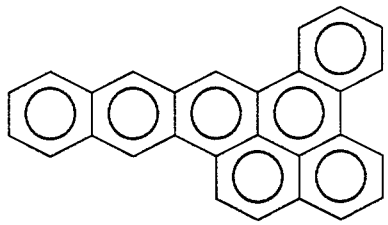

FD-28 Dibenzo[fg,st]pentacene

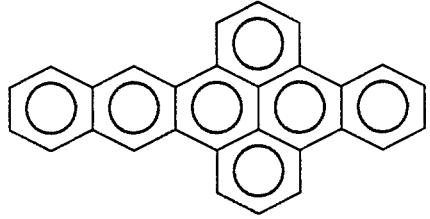

FD-29 Dibenzo[hi,pq]anthanthrene

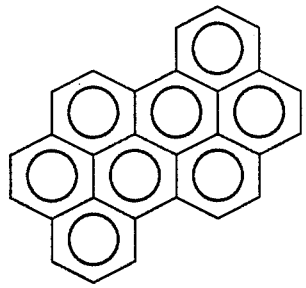

FD-30 Dibenzo[opq,stu]picene

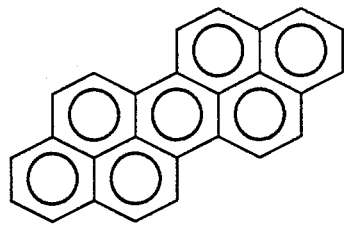

FD-31 Hexacene

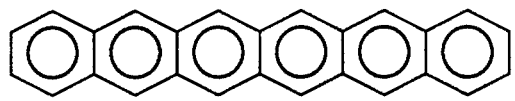

These pentacarbocyclic aromatic rings have the advantage that they can be deposited by vacuum vapor deposition, similarly as the other components of the organic medium. Since the pentacarbocyclic aromatic rings represent chromophores in and of themselves, it is not necessary that other ring substituents be present. However, many dyes containing pentacarbocyclic aromatic rings as chromophores are conventional, having been originally prepared for use in solution chemistry and therefore having substituents intended to modify solubility and, in some instances, hue. Various ring substituents of the pentacarbocylic aromatic rings of the types disclosed by Tang et al (R-2), cited above, are contemplated.

When fluorescent pentacarbocyclic aromatic dyes are incorporated in a formula II host charge acceptor compound in a first category combination, only a small amount of the fluorescent dye is required to realize advantages. Fluorescent pentacarbocyclic aromatic dyes are preferably incorporated in a concentration ranging ranging from 0.05 to 5 mole percent, based on the moles of charge accepting compound. A specifically preferred concentration range is from 0.2 to 3 mole percent, based on the moles of charge accepting compound, with a concentration range of from 0.5 to 2 mole percent, based on the moles of charge accepting compound, being in most instances optimum.

Since it is the potential gradient maintained across the organic medium 208 that is responsible for electroluminescence, constructing the organic EL device with the thinnest possible organic medium allows electroluminescence to be achieved with a minimum potential difference between the anode and cathode of the device. Therefore, the smallest practical thickness of the organic medium is preferred. Typically, the thickness of the organic medium is less than 1 μm, preferably less than 5000 Å. The minimum thickness of the organic medium 208 is determined by the minimum thicknesses of the component zones and layers. To avoid quenching of luminescence the cathode 216 should be separated from the junction 214 by a distance of at least 300 Å—i.e., the electron injecting and transporting zone 212 preferably has a thickness of at least 300 Å. The only remaining constraint on construction dimensions are the minimum layer thicknesses required to assure continuous layers. Each of the layers 218, 220, 222 and 224 has a minimum thickness of at least 20 Å and preferably at least 50 Å. Although the hole injecting and transporting zone 210 can therefore be quite thin, it is preferred that this zone also have a thickness of at least 300 Å.

Among compounds other than the oxines of formula I useful in forming thin films suitable for constructing the electron injecting layer 222 within the preferred thickness ranges are the butadienes, such as 1,4-diphenylbutadiene and tetraphenylbutadiene; coumarins; and stilbenes, such as transstilbene, disclosed by Tang U.S. Pat. No. 4,356,429, cited above.

Still other thin film forming electron injecting and transporting zone compounds which can be used to form the layer adjacent the cathode are optical brighteners, particularly those disclosed by VanSlyke et al U.S. Pat. No. 4,539,507, cited above. Useful optical brighteners include those satisfying structural formulae (IV) and (V):

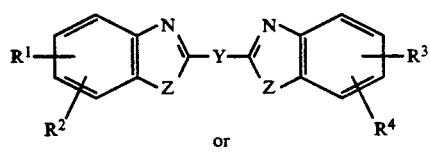

(IV)

or

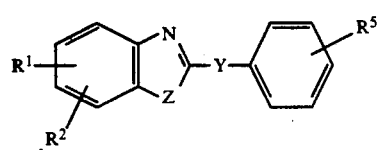

(V)

wherein $R^1$, $R^2$, $R^3$, and $R^4$ are individually hydrogen; saturated aliphatic of from 1 to 10 carbon atoms, for example, propyl, t-butyl, heptyl, and the like; aryl of from 6 to 10 carbon atoms, for example, phenyl and naphthyl; or halo such as chloro, fluoro, and the like; or $R^1$ and $R^2$ or $R^3$ and $R^4$ taken together comprise the atoms necessary to complete a fused aromatic ring optionally bearing at least one saturated aliphatic of from 1 to 10 carbon atoms, such as methyl, ethyl, propyl and the like;

$R^5$ is a saturated aliphatic of from 1 to 20 carbon atoms, such as methyl, ethyl, n-eicosyl, and the like; aryl of from 6 to 10 carbon atoms, for example, phenyl and naphthyl; carboxyl; hydrogen; cyano; or halo, for example, chloro, fluoro and the like; provided that in formula (III) at least two of $R^3$, $R^4$ and $R^5$ are saturated aliphatic of from 3 to 10 carbon atoms, e.g., propyl, butyl, heptyl and the like;

Z is —O—, —NH—, or —S—; and

Y is

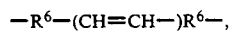

—CH=CH—,

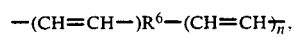

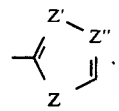

or

wherein m is an integer of from 0 to 4;

n is arylene of from 6 to 10 carbon atoms, for example, phenylene and naphthylene; and Z' and Z" are individually N or CH.

As used herein "aliphatic" includes substituted aliphatic as well as unsubstituted aliphatic. The substituents in the case of substituted aliphatic include alkyl of from 1 to 5 carbon atoms, for example, methyl, ethyl, propyl and the like; aryl of from 6 to 10 carbon atoms, for example, phenyl and naphthyl; halo, such as chloro, fluoro and the like; nitro; and alkoxy having 1 to 5 carbon atoms, for example, methoxy, ethoxy, propoxy, and the like.

Still other optical brighteners that are contemplated to be useful are listed in Vol. 5 of *Chemistry of Synthetic Dyes,* 1971, pages 618–637 and 640. Those that are not already thin-film-forming can be rendered so by attaching an aliphatic moiety to one or both end rings.

In a preferred form of the invention a porphyrinic compound forms the hole injecting layer 218 of the organic EL device 200. A porphyrinic compound is any compound, natural or synthetic, which is derived from or includes the porphyrin structure. Any of the porphyrinic compounds disclosed by Adler U.S. Pat. No. 3,935,031 or Tang U.S. Pat. No. 4,356,429, the disclosures of which are here incorporated by reference, can be employed.

Preferred porphyrinic compounds are those of structural formula (VI):

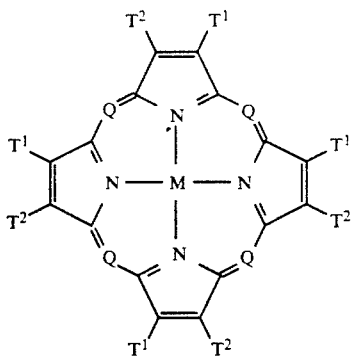

(VI)

wherein

Q is —N= or —C(R)=;

M is a metal, metal oxide, or metal halide;

R is hydrogen, alkyl, aralkyl, aryl, or alkaryl, and $T^1$ and $T^2$ represent hydrogen or together complete a unsaturated 6 membered ring, which can include substituents, such as alkyl or halogen. Preferred alkyl moieties contain from about 1 to 6 carbon atoms while phenyl constitutes a preferred aryl moiety.

In an alternative preferred form the porphyrinic compounds differ from those of structural formula (VI) by substitution of two hydrogens for the metal atom, as indicated by formula (VII):

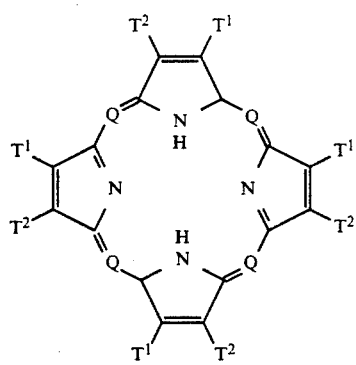

(VII)

Highly preferred examples of useful porphyrinic compounds are metal free phthalocyanines and metal containing phthalocyanines. While the porphyrinic compounds in general and the phthalocyanines in particular can contain any metal, the metal preferably has a positive valence of two or higher. Exemplary preferred metals are cobalt, magnesium, zinc, palladium, nickel, and, particularly, copper, lead, and platinum.

Illustrative of useful porphyrinic compounds are the following:

PC-1: Porphine
PC-2: 1,10,15,20-Tetraphenyl-21H,23H-porphine copper (II)
PC-3: 1,10,15,20-Tetraphenyl-21H,23H--porphine zinc (II)
PC-4: 5,10,15,20-Tetrakis(pentafluorphenyl)-21H,23H-porphine
PC-5: Silicon phthalocyanine oxide
PC-6: Aluminum phthalocyanine chloride
PC-7: Phthalocyanine (metal free)
PC-8: Dilithium phthalocyanine
PC-9: Copper tetramethylphthalocyanine
PC-10: Copper phthalocyanine
PC-11: Chromium phthalocyanine fluoride
PC-12: Zinc phthalocyanine
PC-13: Lead phthalocyanine
PC-14: Titanium phthalocyanine oxide
PC-15: Magnesium phthalocyanine
PC-16: Copper octamethylphthalocyanine The hole transporting layer 220 of the organic EL device 200 preferably contains at least one hole transporting aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al U.S. Pat. No. 3,180,730. Other suitable triarylamines substituted with vinyl or vinylene radicals and/or containing at least one active hydrogen containing group are disclosed by Brantley et al U.S. Pat. Nos. 3,567,450 and 3,658,520.

A preferred class of aromatic tertiary amines are those which include at least two aromatic tertiary amine moieties. Such compounds include those represented by structural formula (VIII):

(VIII)

wherein:

$Q^1$ and $Q^2$ are independently aromatic tertiary amine moieties and

G is a linking group such an arylene, cycloalkylene, or alkylene group or a carbon to carbon A particularly preferred class of triarylamines satisfying structural formula (VIII) and containing two triarylamine moieties are those satisfying structural formula (IX):

(IX)

where $R^1$ and $R^2$ each independently represents a hydrogen atom, an aryl group or alkyl group or $R^1$ and $R^2$ together represent the atoms completing a cycloalkyl $R^3$ and $R^4$ each independently represents an aryl group which is in turn substituted with a diaryl substituted amino group, as indicated by structural formula (X):

(X)

wherein $R^5$ and $R^6$ are independently selected aryl groups.

Another preferred class of aromatic tertiary amines are tetraaryldiamines. Preferred tetraaryldiamines include two diarylamino groups, such as indicated by formula (IX), linked through an arylene group. Preferred tetraaryldiamines include those represented by formula (XI).

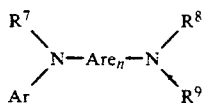

wherein

Are is an arylene group, n is an integer of from 1 to 4, and

Ar, $R^7$, $R^8$, and $R^9$ are independently selected aryl groups.

The various alkyl, alkylene, aryl, and arylene moieties of the foregoing structural formulae (VIII), (IX), (X), and (XI) can each in turn be substituted. Typical substituents including alkyl groups, alkoxy groups, aryl groups, aryloxy groups, and halogen such as fluoride, chloride, and bromide. The various alkyl and alkylene moieties typically contain from about 1 to 5 carbon atoms. The cycloalkyl moieties can contain from 3 to about 10 carbon atoms, but typically contain five, six, or seven ring carbon atoms—e.g., cyclopentyl, cyclohexyl, and cycloheptyl ring structures. The aryl and arylene moieties are preferably phenyl and phenylene Representative useful aromatic tertiary amines are disclosed by Berwick et al U.S. Pat. No. 4,175,960 and Van Slyke et al U.S. Pat. No. 4,539,507. Berwick et al in addition discloses as useful hole transporting compounds N substituted carbazoles, which can be viewed as ring bridged variants of the diaryl and triarylamines disclosed above.

Following the teachings of VanSlyke et al (RPA-5), cited above, it is possible to achieve higher organic EL device stabilities both during short term, and extended operation by substituting for one or more of the aryl groups attached directly to a tertiary nitrogen atom in the aromatic tertiary amines described above an aromatic moiety containing at least two fused aromatic rings. The best combination of both short term (0-50 hours) and long term (0-300+ hours) of operation are achieved when the aromatic tertiary amines are those which (1) are comprised of at least two tertiary amine moieties and (2) include attached to a tertiary amine nitrogen atom an aromatic moiety containing at least two fused aromatic rings. The fused aromatic ring moieties of the tertiary amines can contain 24 or more carbon atoms and preferably contain from about 10 to 16 ring carbon atoms. While unsaturated 5 and 7 membered rings can be fused to six membered aromatic rings (i.e., benzene rings) to form useful fused aromatic ring moieties, it is generally preferred that the fused aromatic ring moiety include at least two fused benzene rings. The simplest form of a fused aromatic ring moiety containing two fused benzene rings is naphthalene. Therefore, the preferred aromatic ring moieties are naphthalene moieties, where the latter is understood to embrace all compounds containing a naphthalene ring structure. In monovalent form the naphthalene moieties are naphthyl moieties, and in their divalent form the naphthalene moieties are naphthylene moieties.

Illustrative of useful aromatic tertiary amines are the following:

ATA-1: 1,1-Bis(4-di-p-tolylaminophenyl)-cyclohexane

ATA-2: 1,1-Bis(4-di-p-tolylaminophenyl)-4-phenylcyclohexane

ATA-3: 4,4'''-Bis(diphenylamino)quaterphenyl

ATA-4: Bis(4-dimethylamino-2-methylphenyl)-phenylmethane

ATA-5: N,N,N-Tri(p-tolyl)amine

ATA-6: 4-(di-p-tolylamino)-4'-[4(di-p-tolylamino)-styryl]stilbene

ATA-7: N,N,N',N'-Tetra-p-tolyl-4,4'-diamino-biphenyl

ATA-8: N,N,N',N'-Tetraphenyl-4,4'-diamino-biphenyl

ATA-9: N-Phenylcarbazole

ATA-10: Poly(N-vinylcarbazole)

ATA-11: 4,4'-Bis[N-(1-naphthyl)-N-phenyl-amino]-biphenyl

ATA-12: 4,4''-Bis[N-(1-naphthyl)-N-phenyl-amino]-p-ter-phenyl

ATA-13: 4,4'-Bis[N-(2-naphthyl)-N-phenyl-amino]-biphenyl

ATA-14: 4,4'-Bis[N-(3-acenaphthenyl)-N-phenylamino]biphenyl

ATA-15: 1,5-Bis[N-(1-naphthyl)-N-phenyl-amino]-naphthalene

ATA-16: 4,4'-Bis[N-(9-anthryl)-N-phenyl-amino]-biphenyl

ATA-17 4,4''-Bis[N-(1-anthryl)-N-phenyl-amino]-p-terphenyl

ATA-18: 4,4'-Bis[N-(2-phenanthryl)-N-phenyl-amino]biphenyl

ATA-19: 4,4'-Bis[N-(8-fluoranthenyl)-N-phenylamino]biphenyl

ATA-20: 4,4'-Bis[N-(2-pyrenyl)-N-phenyl-amino]-biphenyl

ATA-21: 4,4'-Bis[N-(2-naphthacenyl)-N-phenyl-amino]biphenyl

ATA-22: 4,4'-Bis[N-(2-perylenyl)-N-phenyl-amino]-biphenyl

ATA-23: 4'4'-Bis[N-(1-coronenyl)-N-phenyl-amino]-biphenyl

ATA-24: 2,6-Bis(di-p-Lolylamino)naphthalene

ATA-25 2,6-Bis[di-(1-naphthyl)amino]naph-thalene

ATA-26: 2,6-Bis[N-(1-naphthyl)-N-(2-naphthyl)amino]naphthalene

ATA-27: 4,4''-Bis[N,N-di(2-naphthyl)amino]-terphenyl

ATA-28: 4,4'-Bis{N-phenyl-N-[4-(1-naphthyl)-phenyl]-amino}biphenyl

ATA-29: 4,4'-Bis[N-phenyl-N-(2-pyrenyl)-amino]-biphenyl

ATA-30: 2,6-Bis[N,N-di(2-naphthyl)-amine]fluorene

ATA-31: 4,4''-Bis(N,N-di-p-tolylamino)-terphenyl

ATA-32: Bis(N-1-naphthyl)(N-2-naphthyl)amine

The anode and cathode of the internal junction organic EL device can each take any convenient conventional form, such as any of the various forms disclosed by Tang et al U.S. Pat. No. 4,885,211, the disclosure of which is here incorporated by reference. Preferred transparent anodes are formed of a conductive oxide, such as indium tin oxide (ITO). When the anode is not intended to be light transmissive, it can be formed of any of a wide range of metals having a work function of at least 4.0 eV. The preferred cathodes are those constructed of a combination of a metal having a work function less than 4.0 eV and one other metal, preferably a metal having a work function greater can be employed in extremely wide proportions, ranging much <1 percent to >99 percent of the work function metal with another metal, preferably a higher work function metal (e.g., a metal having a work function >4.0 eV), forming the balance of the cathode. The Mg:Ag cathodes of Tang et al U.S. Pat. No. 4,885,211, constitute one preferred cathode construction. Aluminum and magnesium cathodes with magnesium constituting at least 0.05 (preferably at least 0.1) percent and aluminum constituting at least 80 (preferably at least 90) percent constitute another preferred cathode construction. The aluminum and magnesium cathodes are the subject of VanSlyke et al (RPA-1), cited above. Another contemplated cathode construction is disclosed by Scozzafava et al (RPA-4), cited above, wherein the cathode is constructed of fused metal particles containing at least 80 percent indium and a lower work function metal, such as magnesium. In the preferred form the metal particles have a mean diameter of less than 1 $\mu$m and a coefficient of variation of less than 20 percent.

Since cathodes must contain at least one lower (less than 4.0 eV) work function metal to be efficient, cathodes benefit from constructions that protect the lower work function metal from oxidation. It is specifically contemplated to construct the cathode as taught by Littman et al (RPA-2), cited above. In this arrangement the portion of the cathode contacting the organic medium contains at least one metal having work function of <4.0 eV. The cathode additionally includes a capping layer containing at least one alkaline earth or rare earth metal. The metal in the cathode having a work function of <4.0 eV is selected to have a higher work function than the alkaline earth or rare earth metal in the capping layer.

It is additionally contemplated to construct the cathode as taught by VanSlyke (RPA-3), cited above. In this construction the cathode contains at least one metal having a work function of <4.0 eV (other than an alkali metal), and a protective layer overlies the cathode comprised of a metal having a work function in the range of from 4.0 to 4.5 eV and at least one organic component of the organic electroluminescent medium, preferably a stilbene or chelated oxinoid compound.

EXAMPLES

The invention and its advantages can be better appreciated by the following specific examples.

EXAMPLE 1

Blue Emitting Organic EL Device

An organic EL device satisfying the requirements of the invention was constructed in the following manner:

(a) An indium tin oxide (ITO) coated glass substrate was ultrasonically cleaned in a commercial detergent, rinsed in deionized water, degreased in toluene vapor, and exposed to a strong oxidizing agent.

(b) A hole injecting layer of copper phthalocyanine (CuPc) having a thickness of 375 Å was deposited over the ITO on the substrate by vacuum evaporation from a tantalum boat.

(c) Onto the CuPc layer was deposited a 375 Å hole transporting layer of 4,4'-bis[N-(1-naphthyl)-N-phenylamino]-biphenyl, also vacuum evaporated from a tantalum boat.

(d) A blue emitting layer of BA-1 (300 Å) was deposited onto the hole transporting layer. This compound was also vacuum evaporated from a tantalum boat.

(e) Over the BA-1 layer was deposited a 300 Å electron injecting layer of aluminum trisoxine, again by vacuum evaporation from a tantalum boat.

(f) A 2000 Å cathode of a 10:1 atomic ratio of Mg to Ag was formed by vacuum deposition onto the aluminum trisoxine layer to complete the organic EL device.

Figure 4:
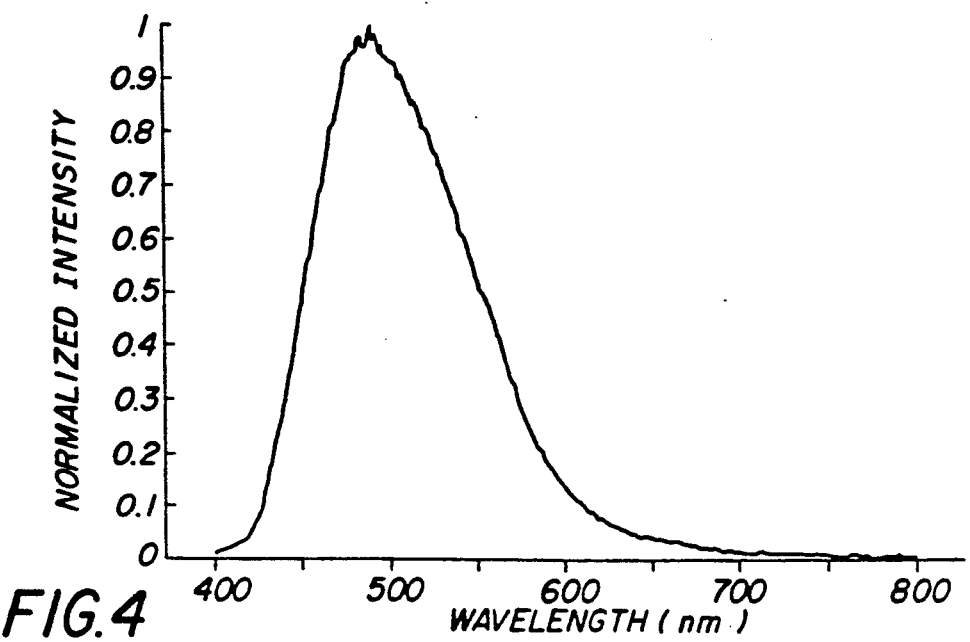
FIG. 4 is a plot of normalized intensity versus wavelength of emission.

In operation, the organic EL device was blue emitting, with peak emission occurring at 490 nm. The spectral emission profile of the organic EL device is shown in FIG. 4. The chromaticity of emission is shown at point E-1 in FIG. 1 (x=0.202; y=0.325).

The electroluminescent efficiency (the ratio of the power of the light emitted by the device to the current, measured at a current density of 20 mA/cm$^2$, was 0.034 W/A. The drive voltage at 20 mA/cm$^2$ was 9.4 volts.

The organic EL device was stability tested with a constant current of 20 mA/cm$^2$. The initial intensity was 0.68 mW/cm$^2$, a level well in excess of that required for practical applications. Light intensity decreased slowly, with a 50 percent reduction after about 55 hours of continuous operation and a 75 percent reduction after 230 hours. This demonstrated a sustained high level of light output.

EXAMPLE 2 AND 3

Varied Blue Emitting Organic EL Devices

Additional organic EL devices were constructed identically as in Example 1, except that BA-1 was replaced by BA-2 or BA-3. Emission peak maxima, EL efficiencies and stabilities are shown in Table I, which also includes Example 1 for comparison. The stabilities of the organic EL devices were comparable to the device of Example 1, showing a half drop in initial light output (ILO) in terms of intensity after about 50 hours and a 75 percent drop after about 250 hours of continuous operation at 20 mA/cm$^2$.

TABLE I

| Example | BA # | Emission Maximum | EL Eff. (w/A) | ILO (hrs) ½ | ILO (hrs) ¾ |
|---|---|---|---|---|---|
| 1 | 1 | 486 nm | 0.034 | 55 | 230 |
| 2 | 2 | 480* | 0.034 | 60 | 263 |
| 3 | 3 | 479* | 0.016 | 68 | 268 |

*The spectrum is essentially identical to FIG. 4, differing only in peak position.

EXAMPLES 4 AND 5

Control Blue Emitting Organic EL Devices

Two EL devices were constructed identically to those in Examples 1 and 3, except that the aluminum trisoxine layer (e) was omitted and the thickness of layer (d) was increased to 600 Å. Both organic EL devices emitted blue light, but with significantly lower electroluminescent efficiencies, compared to the corresponding devices of Examples 1 and 3. The control organic EL devices also required an additional 3 volts to provide a current level of 20 mA/cm$^2$. Device characteristics are summarized in Table II.

TABLE II

| Example # | BA # | Emission Maximum* | EL Eff. (W/A) |
|---|---|---|---|
| 4 | 1 | 490 nm | 0.0094 |
| 5 | 3 | 476 | 0.0092 |

*The spectra are essentially identical to FIG. 4, differing only in peak position.

By comparing Tables I and II the superior performance of the organic EL devices of Examples 1 to 3 inclusive satisfying the requirements of the invention is apparent.

EXAMPLE 6

Control Green Emitting Organic EL Device

An organic EL device was constructed identicaly to that of Example 1, except that the blue emitting layer was omitted and the aluminum trisoxine layer was increased in thickness to 600 Å. The resulting device emitted green light with a maximum emission at 535 nm. The chromaticity of emission is shown at point C-6 in FIG. 1 (x=0.315, y=0.550). The electroluminescent efficiency was 0.022 W/A, substantially less than of the organic EL devices of Examples 1 and 2.

EXAMPLE 7

Control Green Emitting Organic EL Device

Example 6 was repeated, except that aluminum tris(5-methyloxine) was substituted for aluminum trisoxine. The chromaticity of emission is shown at point C-7 in FIG. 1 (x=0.412, y=0.560). Peak emission was at 560 nm. Electroluminescent efficiency was 0.008 W/A. The device emitted yellow green light and with substantially lower efficiencies than the blue emitting devices of Examples 1 to 3 inclusive.

EXAMPLES 8-

Doping to Attain Shorter Wavelengths of Emission

A series of organic EL devices were constructed identically as in Example 1, except that BA-1 was doped with varied amounts of perylene (FD-1), ranging from 0.25 to 4 mole percent, based on BA-1. The results are summarized below in Tables III and IV.

TABLE III

| Example | Mole % Dopant | Emission Maximum | FIG. 1 C.I.E. X | Coord. Y |
|---|---|---|---|---|
| 1 | 0 | 486 nm | 0.20 | 0.33 |
| 8 | 0.25 | 452 | 0.19 | 0.27 |
| 9 | 0.50 | 452 | 0.16 | 0.21 |
| 10 | 1.00 | 452 | 0.16 | 0.21 |
| 11 | 2.00 | 452 | 0.17 | 0.21 |
| 12 | 4.00 | 452 | 0.19 | 0.30 |

From Table III it is apparent that all concentrations of FD-1, ranging from 0.25 to 4 mole per percent, based on BA-1, were effective to shift the emission hues of the organic EL devices of Examples 8 to 12 to shorter wavelengths. The point E-3 in FIG. represents x=0.16, y=0.21. The data indicate that a concentration range of from 0.2 to 3 mole percent is a preferred range, with from 0.5 to 2 mole percent being an optimum range.

TABLE IV

| Example | EL Eff. (w/A) | Volts @ 20 mA/cm$^2$ | ILO mW/cm$^2$ | ½ ILO hrs. |
|---|---|---|---|---|
| 1 | 0.034 | 9.4 | 0.68 | 55 |
| 8 | 0.033 | no meas | 0.66 | 138 |
| 9 | 0.030 | 9.3 | 0.60 | 162 |
| 10 | 0.024 | 9.4 | 0.48 | 275 |
| 11 | 0.023 | 9.1 | 0.46 | no meas |
| 12 | 0.021 | 9.3 | 0.42 | 462 |

Turning to Table IV, it apparent that the overall efficiency of the organic EL devices declines somewhat as the level of dopant increased, but this was more than offset by very dramatic increases in stability being realized.

The invention has been described in detail with particular reference to preferred embodiments thereof, but it will be understood that variations and modifications can be effected within the spirit and scope of the invention.

What is claimed is:

1. An internal junction organic electroluminescent device comprised of, in sequence, an anode, an organic hole injecting and transporting zone, an organic electron injecting and transporting zone, and a cathode, characterized in that said organic electron injecting and transporting zone is comprised of an electron injecting layer in contact with the cathode and, interposed between the electron injecting layer and the organic hole injecting and transporting zone, a blue emitting luminescent layer comprised of a charge accepting compound of the formula:

$$(R^5-Q)_2-Al-O-Al-(Q-R^5)_2$$

where

Q in each occurrence represents a substituted 8-quinolinolato ring nucleus and $R^5$ represents an 8-quinolinolato ring substituent chosen to block sterically the attachment of more than two substituted 8-quinolinolato ring nuclei to any one aluminum atom.

2. An internal device according to claim 1 further characterized in that $R^5$ is a 2-position substituent of the 8-quinolinolato ring nucleus.

3. An internal junction organic electroluminescent device according to claim 2 further characterized in that $R^5$ is an electron donating substituent.

4. An internal junction organic electroluminescent device according to claim 3 further characterized in that $R^5$ is chosen from the group consisting of amino, oxy and hydrocarbon groups containing up to carbon atoms.

5. An internal junction organic electroluminescent device according to claim 4 further characterized in that $R^5$ is a hydrocarbon containing from 1 to 6 carbon atoms.

6. An internal junction organic electroluminescent device according to claim 1 further characterized in that the 8-quinolinolato ring nucleus includes a 4-position ring substituent that is electron donating.

7. An internal junction organic electroluminescent device according to claim 6 further characterized in that the 4-position ring substituent is chosen from among amino, oxy and hydrocarbon groups containing up to 10 carbon atoms.

8. An internal junction organic electroluminescent device according to claim 1 further characterized in that the 8-quinolinolato ring nucleus includes in at least one of its 5,6 and 7 ring positions a substituent that is electron accepting.

9. An internal junction organic electroluminescent device according to claim 8 further characterized in that each of the 5, 6 and 7 ring position electron accepting substituents is chosen from among electron accepting cyano, halogen, and α-haloalkyl, α-haloalkoxy, amido, sulfonyl, carbonyl, carbonyloxy and oxycarbonyl substituents containing up to 10 carbon atoms.

10. An internal junction organic electroluminescent device according to claim 1 further characterized in that the luminescent layer additionally includes a fluorescent dye.

11. An internal junction organic electroluminescent device according to claim 10 further characterized in that the fluorescent dye is chosen to provide a favored recombination site for holes and electrons received from the charge accepting compound and is blue emitting.

12. An internal junction organic electroluminescent device according to claim 11 further characterized in that the blue emitting fluorescent dye exhibits a shorter wavelength emission peak than the charge accepting compound.

13. An internal junction organic electroluminescent device according to claim 11 further characterized in that the blue emitting fluorescent dye contains a stabilizing aromatic chromophoric unit containing at least 5 fused carbocyclic aromatic rings.

14. An internal junction organic electroluminescent device according to claim 13 further characterized in that the chromophoric unit contains from 20 to 40 ring carbon atoms.

15. An internal junction organic electroluminescent device according to claim 14 further characterized in that the fluorescent dye chromophoric unit is chosen from among those containing a perylene, benzopyrene, benzochrysene, benzonaphthacene, picene, pentaphene, pentacene, hexacene or anthanthrene nucleus.

16. An internal junction organic electroluminescent device according to claim 13 further characterized in that the fluorescent dye is present in a concentration ranging from 0.05 to 5 mole percent.

17. An internal junction organic electroluminescent device according to claim 16 further characterized in that the fluorecent dye is present in a concentration ranging from 0.2 to 3 mole percent.

18. An internal junction organic electroluminescent device according to claim 16 further characterized in that the fluorecent dye is present in a concentration ranging from 0.5 to 2 mole percent.

19. An internal junction organic electroluminescent device according to claim 1 further characterized in that the electron injecting and transporting zone and the hole injecting and transporting zone together exhibit a thickness of less than 1 $\mu$m.

20. An internal junction organic electroluminescent device according to claim 19 further characterized in that the organic electron injecting and transporting zone has a thickness of at least 300 Å.

21. An internal junction organic electroluminescent device according to claim 20 further characterized in that the electron injecting layer has a thickness in the range of from 50 to 250 Å.

22. An internal junction organic electroluminescent device according to claim 1 further characterized in that a metal oxinoid compound forms the electron injecting layer.

23. An internal junction organic electroluminescent device according to claim 22 further characterized in that the metal oxinoid compound satisfies the formula:

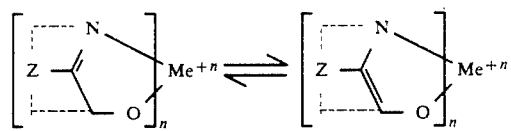

where
Me represents a metal,
n is an integer of from 1 to 3, and
Z represents the atoms necessary to complete an oxine nucleus.

24. An internal junction organic electroluminescent device according to claim 1 further characterized in that the blue emitting compound satisfies the formula:

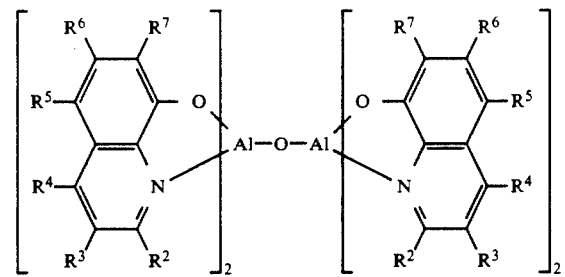

where
$R^2$ represents an electron donating substituent,
$R^3$ and $R^4$ each independently represent hydrogen or an electron donating substituent, and
$R^5$, $R^6$ and $R^7$ each independently represent hydrogen or an electron accepting substituent.

25. An internal junction organic electrluminescent device according to claim 24 further characterized in that the electron donating substituents are independently chosen from the group conssitign of —R', —OR' and —N(R")R', where R' is a hydrocarbon containing up to 6 carbon atoms and R" is hydrogen or R' and the electron accepting substituents are each independently chosen from among electron accepting cyano, halogen, and α-haloalkyl, α-haloalkoxy, amido, sulfonyl, carbonyl, carbonyloxy and oxycarbonyl substituents containing up to 6 carbon atoms.

* * * * *